(12) United States Patent
Campos et al.

(10) Patent No.: US 8,454,546 B2
(45) Date of Patent: Jun. 4, 2013

(54) ORTHOPEDIC DEVICE HAVING A PATIENT COMPLIANCE SYSTEM

(75) Inventors: Michael Campos, Sylmar, CA (US); Chad Leeder, Newbury Park, CA (US); William Arnold, Woodland Hills, CA (US)

(73) Assignee: Ossur HF, Reykjavik (IS)

( * ) Notice: Subject to any disclaimer, the term of this patent is extended or adjusted under 35 U.S.C. 154(b) by 0 days.

(21) Appl. No.: 13/271,629

(22) Filed: Oct. 12, 2011

(65) Prior Publication Data

US 2012/0029402 A1 Feb. 2, 2012

Related U.S. Application Data

(63) Continuation of application No. 12/250,816, filed on Oct. 14, 2008, now Pat. No. 8,043,245.

(60) Provisional application No. 60/960,782, filed on Oct. 15, 2007, provisional application No. 61/071,380, filed on Apr. 25, 2008.

(51) Int. Cl.
*A61F 5/00* (2006.01)
*A43B 23/20* (2006.01)

(52) U.S. Cl.
USPC .................................. 602/27; 36/23

(58) Field of Classification Search
USPC .............. 602/27, 26, 23, 5, 1; 36/23, 66, 163, 36/83, 113, 114, 115, 116, 117.1–125
See application file for complete search history.

(56) References Cited

U.S. PATENT DOCUMENTS

| 2,491,280 | A | | 12/1949 | Roth |
| 4,962,760 | A | | 10/1990 | Jones |
| 5,176,623 | A | * | 1/1993 | Stetman et al. ................. 602/27 |
| 5,250,021 | A | | 10/1993 | Chang |
| 5,370,133 | A | | 12/1994 | Darby et al. |
| 5,370,604 | A | | 12/1994 | Bernardoni |
| 5,399,149 | A | | 3/1995 | Frankowiak |
| 5,445,603 | A | | 8/1995 | Wilkerson |

(Continued)

FOREIGN PATENT DOCUMENTS

| DE | 90 00 405 U1 | 3/1990 |
| EP | 1 504 736 | 2/2005 |

(Continued)

OTHER PUBLICATIONS

Piaggesi et al., "An Off-the-Shelf Instant Contact Casting Device for the Management of Diabetic Foot Ulcers", Diabetes Care, vol. 30, No. 3, Mar. 2007.

(Continued)

*Primary Examiner* — Patricia Bianco
*Assistant Examiner* — Tarla Patel
(74) *Attorney, Agent, or Firm* — Workman Nydegger

(57) ABSTRACT

An orthopedic device includes a strut assembly having a resilient shell defining opposed first and second sides, and a patient compliance system. The patient compliance includes a tightening strap connecting the first and second sides of the shell. The tightening strap has first and second end portions arranged for incremental uni-directional adjustment relative to at least one of the first and second sides of the strut assembly. The tightening strap is arranged to bend the shell and draw the first and second sides thereof toward one another.

15 Claims, 11 Drawing Sheets

U.S. PATENT DOCUMENTS

| | | | |
|---|---|---|---|
| 5,571,077 A | | 11/1996 | Klearman et al. |
| 5,609,570 A | | 3/1997 | Lamont |
| 5,761,834 A | | 6/1998 | Grim et al. |
| 5,865,778 A | | 2/1999 | Johnson |
| 6,024,712 A | * | 2/2000 | Iglesias et al. .................... 602/6 |
| 6,056,712 A | | 5/2000 | Grim |
| 6,080,123 A | * | 6/2000 | Pansiera .......................... 602/16 |
| 6,228,044 B1 | | 5/2001 | Jensen et al. |
| 6,610,897 B2 | | 8/2003 | Cavanagh et al. |
| 6,682,497 B2 | | 1/2004 | Jensen et al. |
| 6,720,470 B2 | | 4/2004 | Cavanagh et al. |
| 6,945,946 B2 | | 9/2005 | Rooney |
| 2002/0029009 A1 | | 3/2002 | Bowman |
| 2002/0095105 A1 | | 7/2002 | Jensen |
| 2002/0128574 A1 | | 9/2002 | Darby |
| 2002/0138030 A1 | | 9/2002 | Darby |
| 2003/0196352 A1 | | 10/2003 | Bledsoe et al. |
| 2003/0199798 A1 | | 10/2003 | Gilmour |
| 2003/0212358 A1 | | 11/2003 | Cavanagh et al. |
| 2003/0216675 A1 | | 11/2003 | Rooney |
| 2004/0103561 A1 | | 6/2004 | Campbell et al. |
| 2004/0111048 A1 | | 6/2004 | Jensen et al. |
| 2004/0168354 A1 | | 9/2004 | Nguyen |
| 2005/0172517 A1 | | 8/2005 | Bledsoe et al. |
| 2005/0240133 A1 | | 10/2005 | Rooney |
| 2006/0030804 A1 | * | 2/2006 | Nordt et al. ....................... 602/26 |
| 2006/0135901 A1 | | 6/2006 | Ingimundarson et al. |
| 2007/0100266 A1 | | 5/2007 | Hargrave et al. |
| 2007/0293798 A1 | * | 12/2007 | Hu et al. .......................... 602/27 |
| 2009/0112134 A1 | | 4/2009 | Avni |
| 2009/0133292 A1 | | 5/2009 | Salvatelli et al. |
| 2009/0177131 A1 | * | 7/2009 | Dar et al. ......................... 602/2 |

FOREIGN PATENT DOCUMENTS

| | | |
|---|---|---|
| EP | 1 593 360 A2 | 11/2005 |
| WO | WO 97/24085 A | 7/1997 |
| WO | WO 2004/009001 A | 1/2004 |
| WO | WO 2008/113321 | 9/2008 |
| WO | 2008/133970 A1 | 11/2008 |

OTHER PUBLICATIONS

M. Myerson, The Total-contact Cast for Management of Neuropathic Planter Ulceration of the Foot, pp. 261-269. Mar. 20, 2007.

Casting, Bureau of Primary Health Care, NHDP. Retrieved Nov. 20, 2007 <http://bphc.hrsa.gov/nhdp/CASTING_PT>.

Total Contact Cast: What It Is and Why It's Used. American Academy of Family Physicians. Nov. 2006.

Calzature taglie forti e ortopediche Optima-Molliter. Retrieved Sep. 27, 2007 <http://www.molliter.com/index.php?intl=eng>.

IPRO 309 Orthotics and Prosthetics Education in Latin America. Retrieved Sep. 27, 2007 <http://www.iit.edu/~ipro309s07>.

International Search Report and Written Opinion in International Application No. PCT/US2008/011694 dated Jun. 18, 2009.

Total Contact Cast What It Is and Why It's Used, American Academy of Family Physicians. Nov. 2006.

Calzature taglie ford e ortopediche Optima-Molliter. Retrieved Sep. 27, 2007 <http://www.molliter.com/index.php?intl=eng>.

IPRO 309 Orthotics and Prosthetics Education in Latin America. Retrieved Sep. 27, 2007 <http://www.ilt.edu/~ipro309s07>.

International Search Report and Written Opinion in International Application No.

* cited by examiner

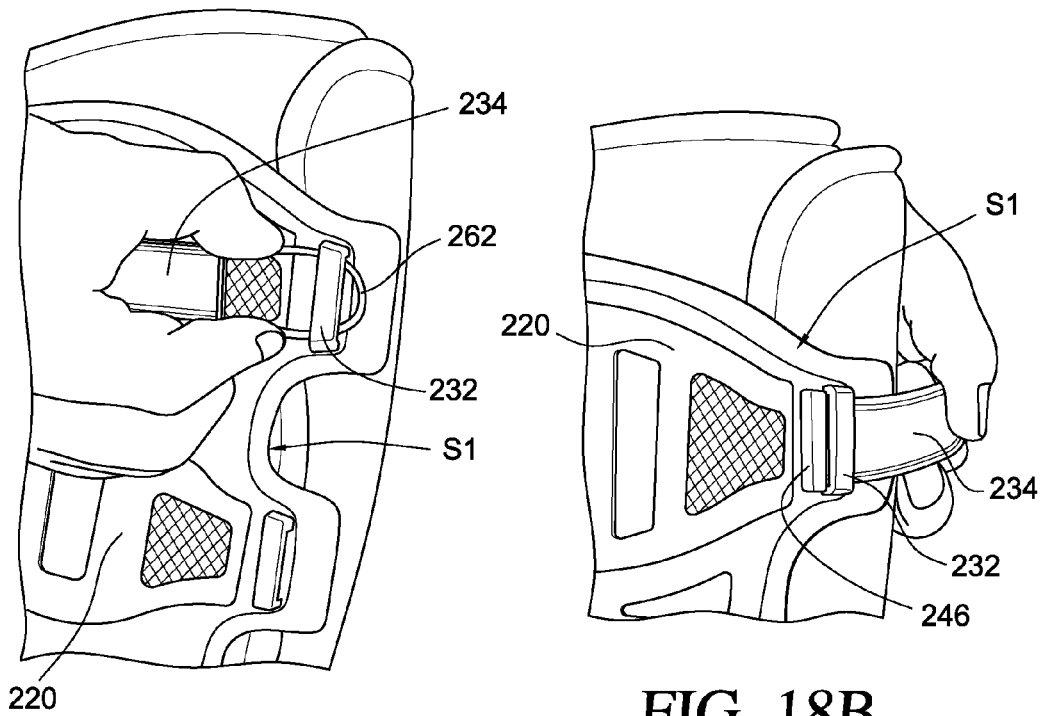
FIG. 18A
FIG. 18B
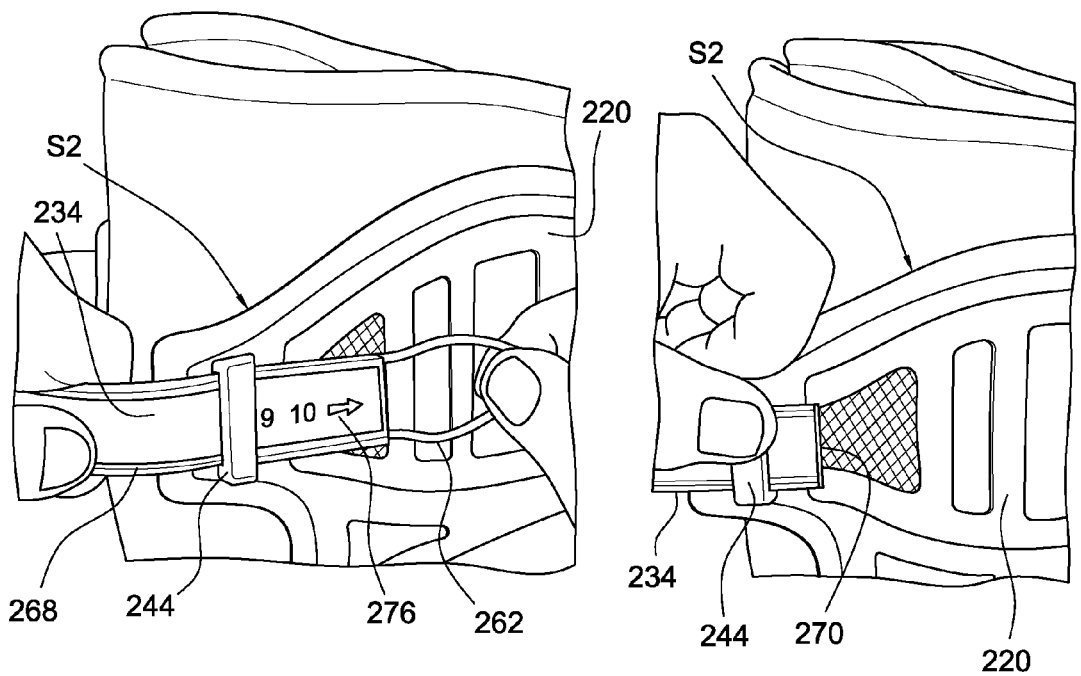
FIG. 18C
FIG. 18D

ORTHOPEDIC DEVICE HAVING A PATIENT COMPLIANCE SYSTEM

CROSS-REFERENCE TO RELATED APPLICATIONS

This application is a continuation of U.S. application Ser. No. 12/250,816, filed on Oct. 14, 2008, now U.S. Pat. No. 8,043,245, which claims the benefit of priority of U.S. provisional applications 60/960,782 filed on Oct. 15, 2007, and 61/071,380 filed on Apr. 25, 2008.

FIELD OF THE INVENTION

The present invention relates generally to the field of orthopedic devices, and more particularly to an orthopedic device in the exemplary form of a cast walker allowing easy access to tissues adjacent to or covered by the walker, and forcing patient compliance in wearing the walker throughout the duration of treating a wound.

BACKGROUND

Foot ulcers represent one of the most notable risk factors for lower extremity amputations in persons diagnosed with diabetes mellitus, a disorder in which blood sugar (glucose) levels are abnormally high because the body does not produce enough insulin. Persons diagnosed with diabetes are typically classified as slow healers and are prone to debilitating foot ulcers due to both neurological and vascular complications.

Peripheral neuropathy, or a deadening of the nerves, can cause altered or complete loss of tactile sensation in the foot and/or leg, and in this regard, the diabetic patient with advanced neuropathy tends to loose the ability to discriminate between sharp-dull tactile sensations. Accordingly, any cuts or trauma to the foot of a diabetic patient with advanced neuropathy often go unnoticed for lengthy periods of time, and may develop into neuropathic ulcers.

Further, a deformity commonly known as "charcot foot" occurs as a result of decreased sensation. Patients with "normal" tactile sensation in their feet automatically determine when too much pressure is being placed on an area of the foot. Once identified, the human body instinctively shifts position to relieve the stress. A patient with advanced neuropathy looses this important mechanism. As a result, tissue ischemia and necrosis, or a restriction in blood supply or a deadening of the tissue, may occur and thus lead to plantar ulcers. Microfractures in the bones of the foot thus may go unnoticed and untreated, resulting in disfigurement, chronic swelling and additional bony prominences.

Microvascular disease is an additional problem for diabetic patients, which can also lead to foot ulcers. It is well known that diabetes often results in a narrowing of smaller arteries, which narrowing cannot be resolved surgically. This microvascularization thus further prompts the diabetic patient to adhere to a strict glucose level regimen, maintain an ideal body weight and cease tobacco smoking in an attempt to reduce the onset of microvascular disease.

Should a diabetic patient develop a plantar ulcer, for whatever reason, treatment options are generally limited to a twofold treatment plan. In the first instance, the prime objective is to obtain wound closure, which eliminates a portal of entry for bacterial invasion and development of limb-threatening infection. In the second instance, a further objective is to allow for a reduction in pressures on the foot or the "off-loading" of tissues. In this regard, protective orthotic footwear has been shown to lower sited foot pressures and further has been shown to contribute to the healing and closing of wounds. Moreover, once a given plantar ulcer has been effectively closed, protective orthotic footwear has been shown to prevent the reoccurrence of plantar ulcers.

A number of factors guide the selection of the appropriate off-loading modality for a particular patient. A few of these factors are patient compliance, comfort, ease of application, and cost. Common methods of off-loading plantar ulcers are the use of total contact casts (TCC) or lower leg walking boots otherwise known as removable cast walkers (RCW).

Removable cast walkers are often chosen in order to reduce application time and to allow the clinician to have easy access to the wound site for wound care procedures. Exemplary walkers are disclosed in U.S. Pat. Nos. 5,078,128, granted January 1992, 5,329,705, granted July 1994, and 5,378,223, granted Jan. 3, 1995, and in U.S. publication nos. 2004/0019307 and 2007/0293798, and all incorporated herein by reference. Walkers are usually quite easy to apply and remove, typically utilizing straps with VELCRO (hook and loop fasteners) or buckles.

However, the same ease with which a clinician may remove the walker in order to inspect and treat the wound site also allows patients to remove the walker outside of the presence of the clinician. Thus one concern with the use of walkers is that the healing of the ulcer will be severely compromised by patients removing the walker and ambulating without the product applied. A clinician is thus left to wonder with each application of a walker whether the patient will follow the advice of the clinician or whether the healing will be compromised by the patient removing the walker. Studies done by members of this research team and others have suggested that patients with plantar wounds secondary to diabetes only wear their off-loading device for an average of 28 percent of their daily activity.

As discussed in the paper "Evaluation of Removable and Irremovable Cast Walkers in the Healing of Diabetic Foot Wounds: A Randomized Controlled Trial," by D. G. Armstrong et al. in *Diabetes Care* 28:551-554, 2005, the TCC has generally been considered the gold standard for off-loading plantar ulcers in part because it is not removable by patients. The concept of utilizing the total contact cast to treat plantar ulcers was developed in the 1950's. The total contact cast must be applied and removed by a clinician in a number of steps, as will be understood by the skilled artisan. The application is time consuming, since an inner shell of casting tape must by applied and allowed to fully dry, and then an exterior shell of casting tape is applied.

The exterior shell must typically be allowed to dry for a full 24 hours before a patient can put any weight on the TCC. Additionally, the TCC must be removed at least once every one to two weeks, if not more frequently, so that the clinician can inspect and treat the plantar ulcerations. Of course, removal of the TCC requires another application of a TCC. Thus, it seems that the use of walkers is a more efficient and economic manner of treating plantar ulcerations.

As for RCWs, while they have been have been found to be easy to use and safe to apply, a significant drawback is that patients can remove the RCW. Further, it has been found that patient compliance to these removable devices is poor. In order to force the patients to wear the RCWs, it has been proposed by D. G. Armstrong et al. to use a RCW and render it irremovable by the application of a single-layer fiberglass band. This prevents the patient from removing the RCW without notification to the clinician. Alternative methods include using a lace which can only be removed by being cut off by a tool, thereby serving as notice to the clinician that the patient has indeed removed the RCW.

From these observations, it is clear that there is a need for a device that allows easy access to wounds on the foot or ankle without removal and reapplication of the entire device. Accordingly, a RCW allowing easy access to wounds on the foot or ankle of a patient is provided that solves these and other problems associated with previous designs.

Further, there is also a need for a device that forces compliance of a walker, while still maintaining many of its benefits such as ease of application, safety of use, reduction of costs, and universality of a product. Thus, there is a need for a walker having a forced patient compliance system.

SUMMARY

As discussed above, current orthopedic devices typically require a clinician to remove the entire apparatus from the patient in order to inspect and treat wounds on the patient's foot and ankle. While these devices provide improved patient compliance, they are also relatively expensive and time consuming to apply. Further, due to the requirement that the wounds be checked weekly, or sometimes daily, the repeated removal and application or reapplication of an orthopedic device also adds to the costs involved in treatment.

Accordingly, walkers with removable or detachable bases and/or sole areas that allow the inspection and treatment of the foot or ankle are proposed. In a typical walker, there are two main components: the base/sole and strut. The base/sole component is the area that surrounds and supports the foot when the walker is in use. The strut component involves the strapping system or any apparatus used to secure the leg to the strut(s) to immobilize the leg.

In order to allow a clinician easy access to the foot and ankle, the walker has a movable or a removable/detachable base and/or sole area that allows the practitioner access to the plantar surface of the foot without requiring removal of the strut component from the patient's leg. In other words the strut component remains on the patient's leg when the base/sole area is removed. Thus, the clinician is not required to completely remove and replace, or to remove and reapply the orthopedic device. Accordingly, the time required for each patient visit can be greatly reduced, as well as reducing the costs associated with the treatment.

Another significant issue regarding walkers is the low level of compliance by the patient. Because of their configuration, most walkers are readily removable by the patient. This creates the problem in that the patient may prematurely or frequently remove the walker, thereby disrupting the healing process of the foot.

As has been proposed, walkers having devices which force the patient to comply with wearing the walker have been shown to be an effective means for treating wounds of the foot and ankle. From this, embodiments according to the invention include devices which force the patient to comply with the wear requirements of the walker. These devices, however, transcend simply securing and forcing patient adherence of the walker, but they also assist in providing effective and versatile securing of the walker on the patient in order to accommodate a variety of leg and foot sizes.

In accordance with one embodiment, a walker comprises a base having an outsole, and first and second side supports extending from the outsole. First and second struts are hingedly linked to the first and second side supports, respectively, and are received by the first and second side supports, respectively, when in a locked position. A locking device is connected to each of the first and second side supports, and the first and second struts, respectively. The locking device selectively permits rotation of the struts relative to the side supports.

The locking device allows for the struts to be connected to the side supports in a hinged manner which allows for maintaining the struts on the leg of the patient so the walker may be removed from the patient at least at the area of the foot. In order to assist the hinging of the struts relative to the side supports, a hinge device may be provided which connects the struts to the side supports. The hinge device is arranged to permit withdrawal of the struts from the side supports, and rotation of the struts relative to the side supports.

A shell may be secured to a respective strut and have a plurality of side wings which generally extend lateral relative to the strut. The shell may be configured to be resilient relative to the strut which is preferably substantially rigid. The shell may be ventilated by the provision of a plurality of slots or apertures which provide a circulation of air therethrough. The shell may also include a plurality of brackets located on the side wings which are configured for receiving a tightening mechanism. Furthermore, the shell preferably has wings which extend to both the anterior and posterior portions of the walker, thereby embracing both front and rear portions of the leg, while leaving portions thereof untouched.

In a variation of the shell, a shell has first and second sides, a resilient rear portion connecting the first and second sides to one another, and an open frontal portion defining a clearance between the first and second sides. The shell comprises at least one main shell body and a border portion. The rear and border portions have greater flexibility properties than the at least one main shell body. A pair of substantially rigid frame members may be secured to the first and second sides of the shell.

From this variation, the resilient rear portion of the shell advantageously permits the two sides along the front portion of the shell to be drawn towards one another with a strap or other form of a tightening mechanism. The rear portion and the border portion also advantageously are more compliant than the main shell bodies, thereby permitting some compliance to the wearer's leg. The rigid frame members may be embedded in the shell such as by overmolding, so as to provide a rigid reinforcing structure and thereby prevent twisting of the leg when a walker is secured thereon.

In order to provide for better patient compliance of the walker, a plurality of tightening bands may be secured to and extend between the struts. Unlike in conventional walkers, however, these tightening bands preferably lock to or are fixably retained by the walker. In other words, these tightening bands may be tightened by the patient, but cannot be removed by the patient without their destruction.

According to one variation, the tightening bands are generally secured to and extend from the first strut to the second strut. Preferably, the tightening bands pass through and are secured to the brackets carried by the side wings. Because the side wings are generally resilient, upon tightening of the tightening bands, the shells may be drawn closer to the leg of the patient to assure a more secure and tighter fit. The embodiments described herein are particularly advantageous since there are tightening bands provided on both the anterior and posterior aspects of the walker, thereby permitting better adjustment to the particular geometry of the leg.

In one variation, the tightening bands are incrementally adjustable relative to the first and second struts at a plurality of substantially uniform settings. This result may be obtained by forming a ratcheting device by the combination of a plurality of teeth located on the tightening bands, and a detent carried by the brackets. From this ratcheting device, end portions of the tightening bands are only uni-directionally adjustable relative to the corresponding brackets, this direction being solely in direction which tightens the walker on the leg.

Preferably, the tightening bands are formed from a material that permits the bands to be broken with a cutting instrument. In addition, the tightening bands may be formed in a manner to assure secure fastening relative to the brackets, comfortably spanning the distance between the struts and side supports of the leg or foot, and easy tightening by way of enlarged portions. A center portion of the tightening band is preferably of reduced material so as to facilitate cutting of the bands by a cutting instrument.

In a variation of the tightening band, the tightening band is elongate and formed with a resilient and deformable handle, a base sized larger than a bracket or mount located on the strut assembly, and a plurality of teeth formed along one side. The tightening band forms at least one rib on a second side thereof which is configured to correspond to channels formed in the bracket or mount on the strut assembly.

The numerous advantages, features and functions of the various embodiments of a cast walker with easy access to a wound site will become readily apparent and better understood in view of the following description and accompanying drawings. The following description is not intended to limit the scope of the walker with easy access to a wound site and forced patient compliance, but instead merely provides exemplary embodiments for ease of understanding.

BRIEF DESCRIPTION OF THE DRAWINGS

FIGS. 18A-18D are schematic views showing the installation of the tightening band on the orthopedic device according to FIG. 12.

Figure 1:
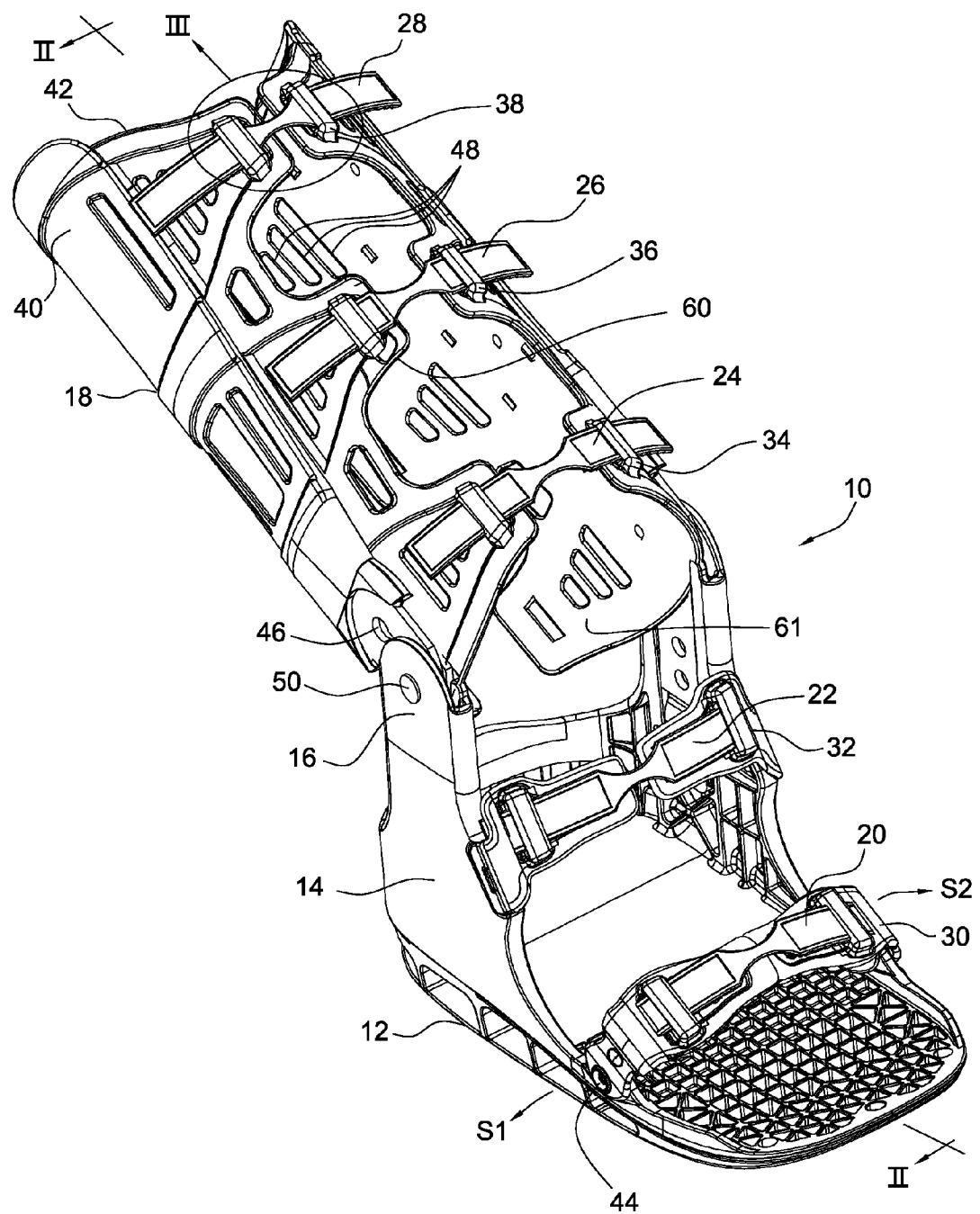
FIG. 1 is a perspective view of an embodiment of an orthopedic device having a patient compliance system.

In the various figures, similar elements are provided with similar reference numbers. It should be noted that the drawing figures are not necessarily drawn to scale, but instead are drawn to provide a better understanding of the components thereof, and are not intended to be limiting in scope, but rather provide exemplary illustrations.

DETAILED DESCRIPTION OF VARIOUS EMBODIMENTS

Figure 2:
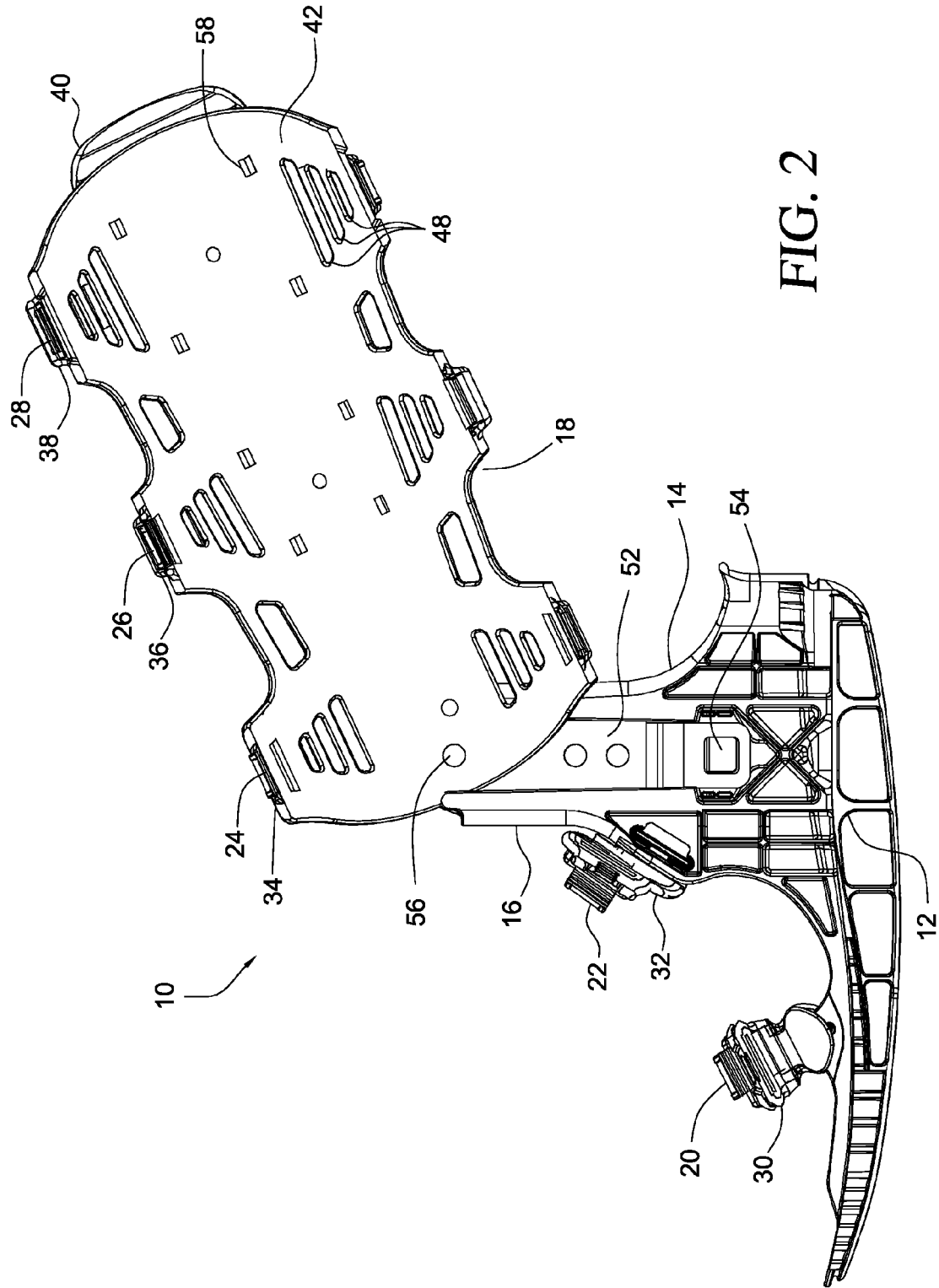
FIG. 2 is a cross-sectional view of the embodiment of FIG. 1 taken along line II-II.

An embodiment of a walker having many of the aforementioned attributes is disclosed in FIGS. 1 and 2. The walker 10 may be constructed in a manner similar to conventional walkers, such as those described in detail in U.S. Pat. Nos. 5,078,128, 5,329,705, and 5,378,223, U.S. publication nos. 2004/0019307 and 2007/0293798, all incorporated herein by reference.

In particular, the walker 10 has at least one strut member 18 that extends vertically from and is hingedly connected to side supports 16 of a base 14 of the walker. A typical configuration has two opposed strut members 18 that extend in the proximal direction from opposed sides of a base, or from two opposed bases. The base 14 has a foot receiving portion 12 that extends in the anterior and posterior directions, and is shaped and configured to receive and support a patient's foot therein. The struts 18, side supports 16 and base 14 may be made of any suitable rigid or semi-rigid material, for example aluminum, carbon/epoxy composites, glass fiber/epoxy composites, or plastic materials.

The terms "rigid" and "flexible" may be used herein to distinguish characteristics of portions of certain features of the orthopedic device. The term "rigid" is intended to denote that an element of the support is generally devoid of flexibility. Within the context of support members that are "rigid," it is intended to indicate that they may break if bent with sufficient force. On the other hand, the term "flexible" is intended to denote that features are capable of repeated bending. The term "resilient" is used to qualify such flexible features as generally returning to the initially molded shape without permanent deformation. As for the term "semi-rigid," this term is used to connote properties of support members that provide support and are free-standing, however such support members may have some degree of flexibility or resiliency.

At the base 14, a patient compliance system is provided in the exemplary form of lower and upper tightening bands 20, 22 which are secured to lower and upper brackets 30, 32, and located on corresponding first and second sides S1, S2 of the base 14. The brackets 30, 32 may be removably secured to the base 14. In order to provide added versatility and patient accommodation, the lower bracket 30 may be pivotally secured to the base 14 at pivot point 44.

The tightening bands 20, 22 are fixably secured to the lower and upper brackets 30, 32, and may be only adjusted at their end portions at the corresponding sides S1, S2. As such, each end of the tightening bands is only uni-directionally adjustable in corresponding directions, S1, S2. In effect, the brackets 30, 32 form ladder ratchets with the tightening brands 20, 22. It will be noted that while all of the brackets are shown in combination with tightening bands, other means may be used to secure the walker onto the leg. For example, suitable circumferential straps, readily known to the skilled artisan, having hook and loop fastening material may be used in place of any of the tightening bands.

The struts 18 include strut frames 40 upon which a flexible shell 42 is secured. A shell 42 is preferably secured to the internal aspect of the respective strut frame 40. The shell 42 includes a series of anterior and posterior side wings 60, 61 which extend along the length of the shell 42 and laterally relative to the strut frame 40. The shells 42 are preferably ventilated with slots or apertures 48 which make the shells more breathable for the patient. The shells 42 preferably are detachably secured to the strut frames 40 by a plurality of brackets 58 but may alternatively be formed integrally with the strut frames.

The side wings 60, 61 each include a bracket 34, 36, 38 through which tightening bands 24, 26, 28 extend and are secured therewith. As with the brackets 30, 32 and tightening bands 20, 22, the brackets 34, 36, 38 form ratchets with the corresponding tightening brands 24, 26, 28.

The strut 18 is secured to the side supports 16 via a hinge device 46 which connects to a frame member 52 housed within the side supports 16 and the base 14. The frame member 52 locks to the base 14 via a locking mechanism 54. Examples of the locking mechanism 54 are found in U.S. patent application publication 2007/0293798.

The hinge device 46 permits the struts 18 to be rotated relative to the base 14 of the walker. This allows for the struts 18 to remain secured on the patient, while the tightening bands or similar tightening devices are removed from the walker on the base to allow for inspection of the foot. By hinging the walker, a clinician can more easily inspect the leg while allowing for comfort to the leg of the patient since the ankle is essentially made free from the strut portion of the walker.

In order to retain the strut 18 in a fixed position, a locking device 50 is provided at the hinge device 46 in order to retain the strut 18 in an upright position relative to the side strut support 16. The locking device 50 includes a pivot point 56 about which the strut 18 is pivotable relative to the side support 16.

Figure 3:
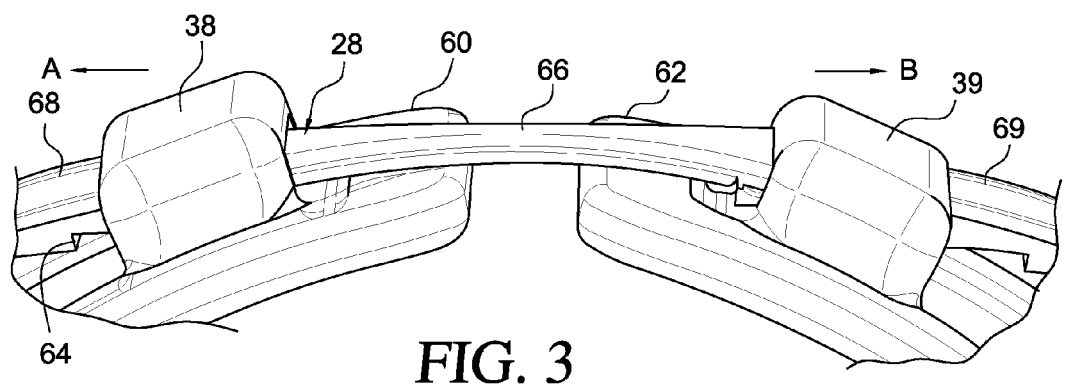
FIG. 3 is a sectional view taken from the embodiment of FIG. 1 at section III.
Figure 4:
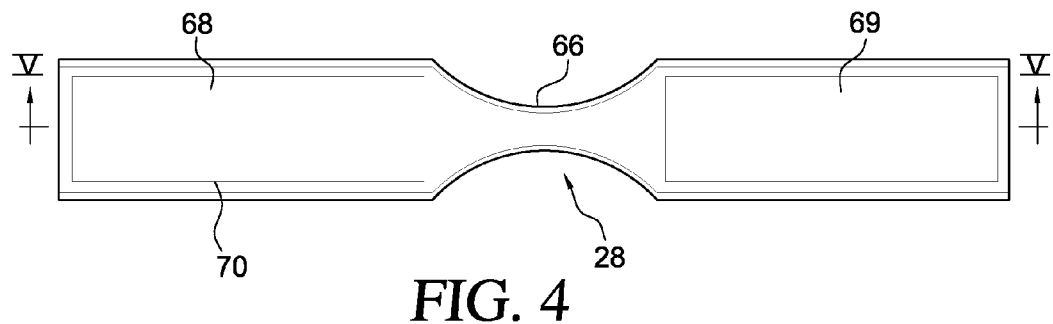
FIG. 4 is a plan view of an embodiment of a tightening band.
Figure 5:
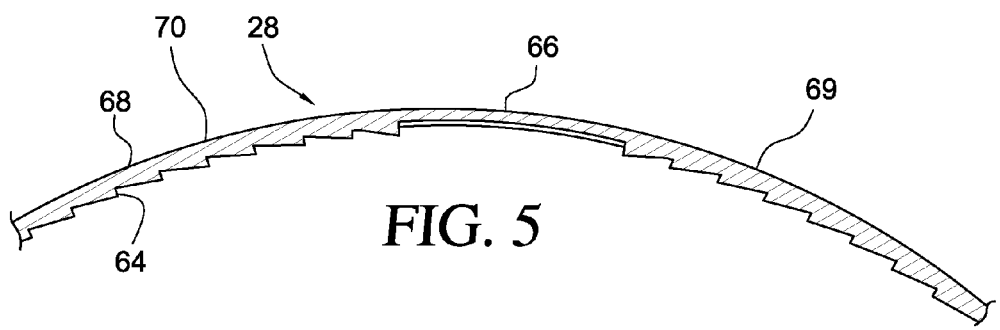
FIG. 5 is a cross-sectional view of the embodiment of FIG. 4 taken along line V-V.

In turning to FIGS. 3-5, an embodiment of the tightening band 28 is shown. FIG. 3 exemplifies the tightening band 28 as having first and second ends 68, 69 which are secured to brackets 38, 39 carried by opposed first and second wings 60, 62 of the shell 42. The wings 60, 62 are configured in part to extend between first and second sides of the walker, and cover the leg, as the tightening band extends thereover. The first and second ends 68, 69 of the tightening band 28 are arranged relative to the brackets 38, 39 so as to be pulled in directions of the sides S1, S2, respectively. As the ends 68, 69 are pulled, the flexibility of the wings 60, 62 are drawn towards one another so as to generally secure the shell to the leg.

The tightening band 28 includes a central portion 66 that has a reduced material geometry that facilitates cutting of the tightening band. The tightening band 28 also includes enlarged portions 70 located at the end portions which facilitate pulling the ends 68, 69 through the brackets 38, 39. Further, the tightening band 28 defines a plurality of serrations or teeth 70 which are used to engage with the brackets 38, 39.

The central portion is also advantageously configured so as to allow for greater flexibility of the tightening band in situations where a leg (such as a larger sized leg) bends the brackets located on the wings into an angular portion. For example, it has been found that when a leg is inserted into the walker, the wings extend around the leg in a position that bends the brackets downwardly. To illustrate this phenomenon, when a leg in not in the walker, the brackets of the walker are generally configured in a straight configuration exemplified by | |. On the other hand, when the leg is placed in the walker, the brackets resemble the configuration exemplified by \/. Hence, the reduced material geometry imparts greater flexibility to the tightening bands without breaking the brackets when the brackets are bent.

The tightening band may be constructed from a variety of materials, in particular polymeric materials which afford sufficient flexibility and resilience to engage with the brackets, while having sufficient toughness to retain the walker on the leg and foot of the patient. The tightening band may be modified so that it is incrementally positionable in a variety of directions or merely uni-directionally.

Figure 6:
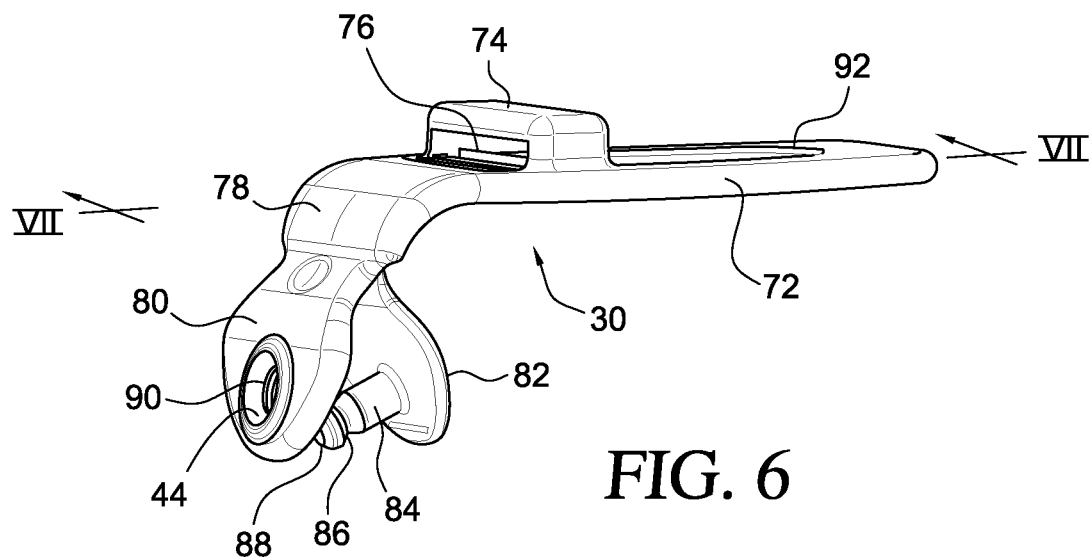
FIG. 6 is a perspective view of an embodiment of a bracket for use with the tightening band of FIG. 4.
Figure 7:
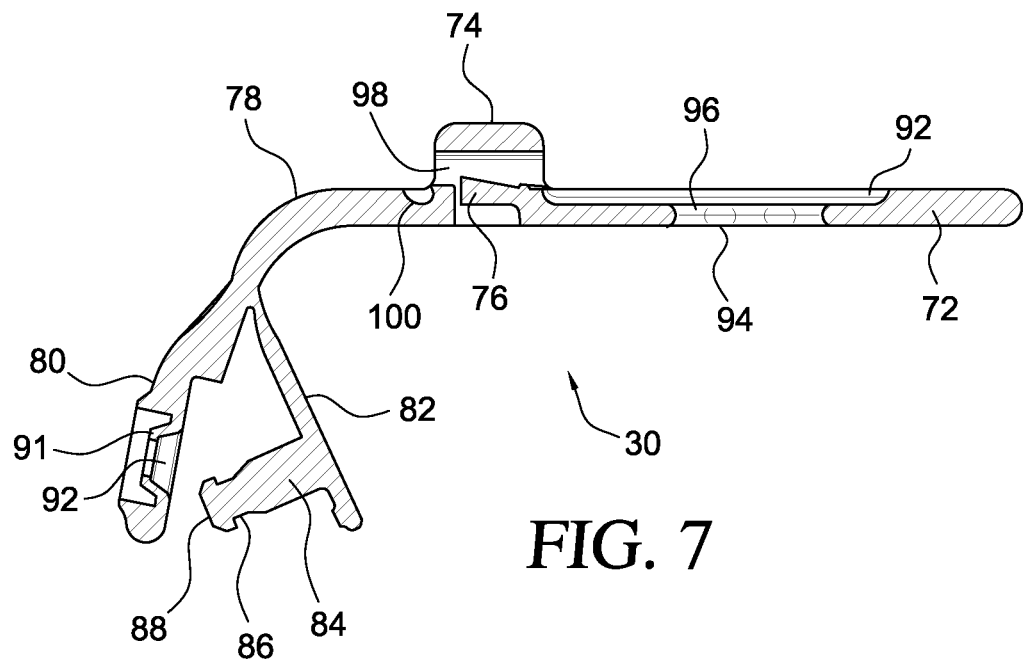
FIG. 7 is a cross-sectional view of the embodiment of FIG. 6 taken along line VII-VII.

In observing FIGS. 6 and 7, an embodiment of a lower bracket 30 is depicted which may be mounted on the lower portion of the base 14 of the walker shown in FIG. 1. The bracket 30 defines an elongate portion 72 merging into a bend 78 upon which corresponding outer and inner clasps 80, 82 extend therefrom. A retainer 74 is connected to the elongate portion 72 and defines a passageway 98 therethrough that is sized and configured for permitting the passage and engagement of a tightening band. A detent 76 extends from the elongate portion so as to engage with the teeth of the tightening band due to the size constraints of the passageway 98, thereby serving as a ratchet means.

The outer and inner clasps 80, 82 are formed to engage one another, wherein the inner clasp 82 carries a pin 84 having a head 88 and a notched portion 86 located below the head 88. The pin 84 is configured to extend through and engage an opening 90 formed through the outer clasp 80. The opening 90 includes an internal rim 91 that is engaged by a notch 86 when the clasps 80, 82 are closed towards one another. When installed on the walker, the pin 84 extends through an opening 124 (see FIGS. 10 and 11) formed on the walker and is fixed therewith as the clasps are closed towards one another.

The elongate portion 72 is intended to extend across or over the foot when the brackets are secured to mutually opposed sides of the base. In order to provide a circulation of air, the elongate portion includes a plurality of ribs 94 which space a plurality of openings 96.

Figure 8:
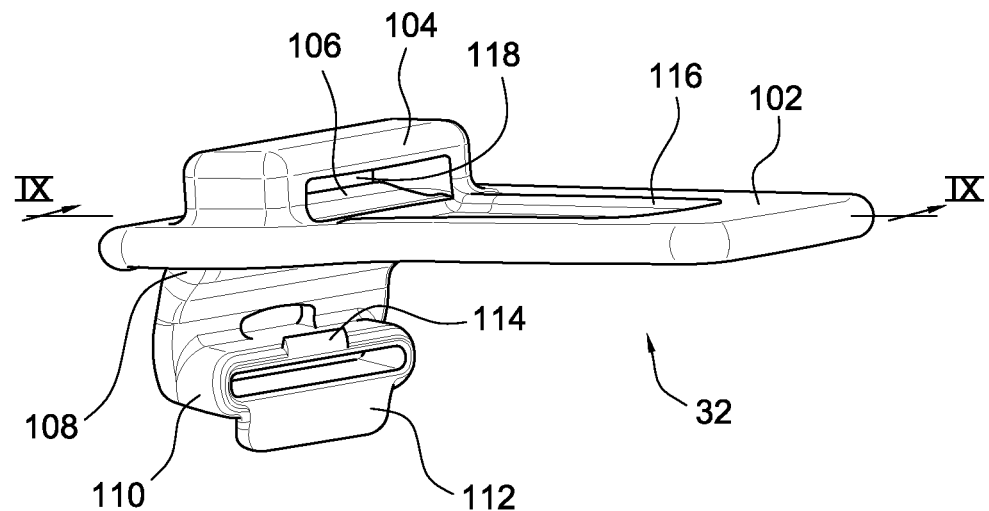
FIG. 8 is a perspective view of another embodiment of a bracket for use with the tightening band of FIG. 4.
Figure 9:
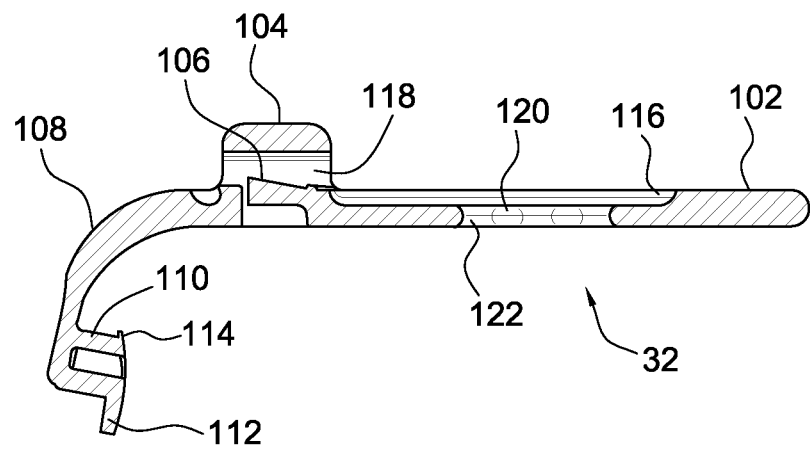
FIG. 9 is a cross-sectional view of the embodiment of FIG. 8 taken along line IX-IX.

In observing FIGS. 8 and 9, an embodiment of the upper bracket 32 is disclosed. As with the lower bracket 30, the upper bracket 32 defines an elongate portion 102 with a retainer 104 provided thereon. A detent 106 extends from the elongate portion 102 into a passageway 118 formed defined between the retainer 104 and the elongate portion 104. The detent 106 is sized and configured to engage the serrations or teeth of the tightening band.

The upper bracket 108 defines a bend 108 connecting the elongate portion 102 to an arm 110 which extends below the elongate portion 102. The arm 110 has an end portion which forms a lower flange 112 and an upper lip 114. The lower flange 112 and the upper lip 114 are sized and configured to be insertable through a slot 126 (see FIGS. 10 and 11) formed along side portions of the base of the walker, and engage therewith.

As with the lower bracket 30, the upper bracket 32 is arranged to extend over the foot, and generally conform therewith when the tightening band is inserted and engages opposed upper brackets 32. The elongate portion 102 defines a recessed portion 116 that includes a plurality of ribs 120 with openings 122 defined therebetween.

The upper and lower brackets, as with the shell, may be formed from a plurality of materials, such as polymeric materials. Each bracket is preferably integrally molded as a unity piece.

Figure 10:
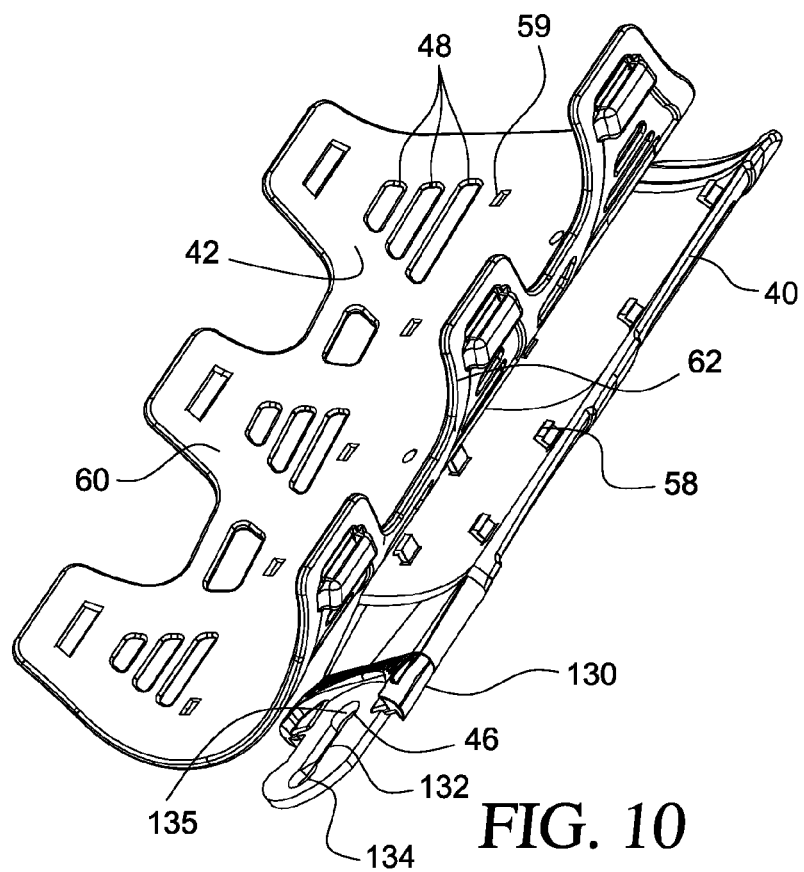
FIG. 10 is an exploded perspective view of a variation of a strut and shell shown in FIG. 1.

In the embodiment of FIG. 10, the shell 42 is preferably detachable from the strut frame 40 via locking protrusions 58 formed on the strut frame 40 and interlocking with corresponding apertures 59 formed on the shell 42. This embodiment allows for the strut frame 40 to have different properties (i.e., resiliency) from the shell 42. According to other embodiments, the shell 42 is overmolded onto the strut frame 40 using processes and materials more specifically disclosed in U.S. patent application publication 2007/0293798. The shell 42 is formed with resilient materials thereby permitting first and second sides thereof to bend toward one another with a tightening mechanism. The hinge device 46 located at the lower end of the strut frame 40 includes an elongate slot 132 extending between openings 134, 135 enlarged in size greater than the width of the slot 132 in order accommodate the locking device 50, as shown in FIG. 1. The openings 134, 135 open into the slot 132 and the peripheries are delimited by material of the hinge device at areas outside the slot.

Figure 11:
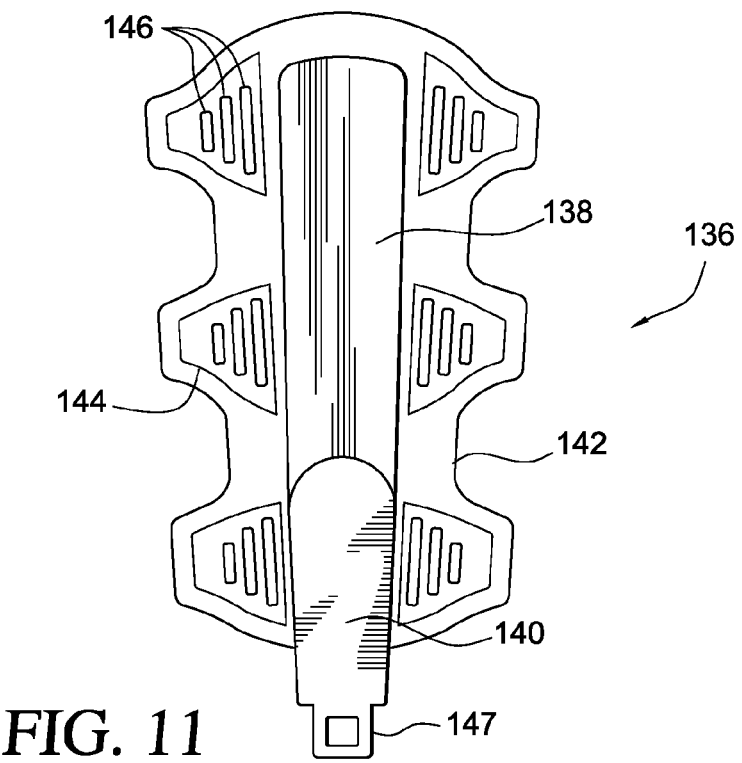
FIG. 11 is an elevational view of another variation of a strut and shell.
Figure 12:
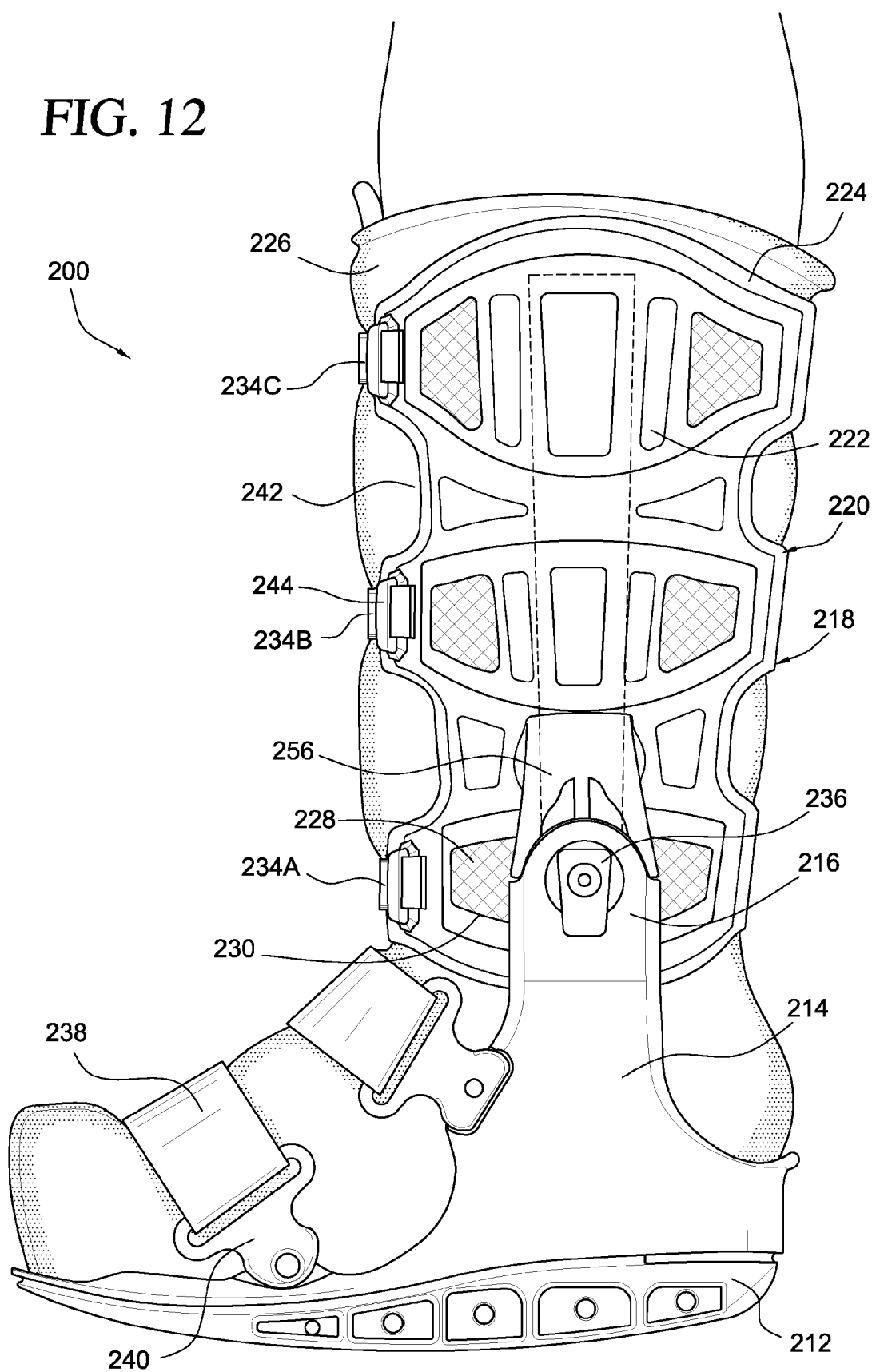
FIG. 12 is a perspective view of another embodiment of an orthopedic device having a patient compliance system.
Figure 14:
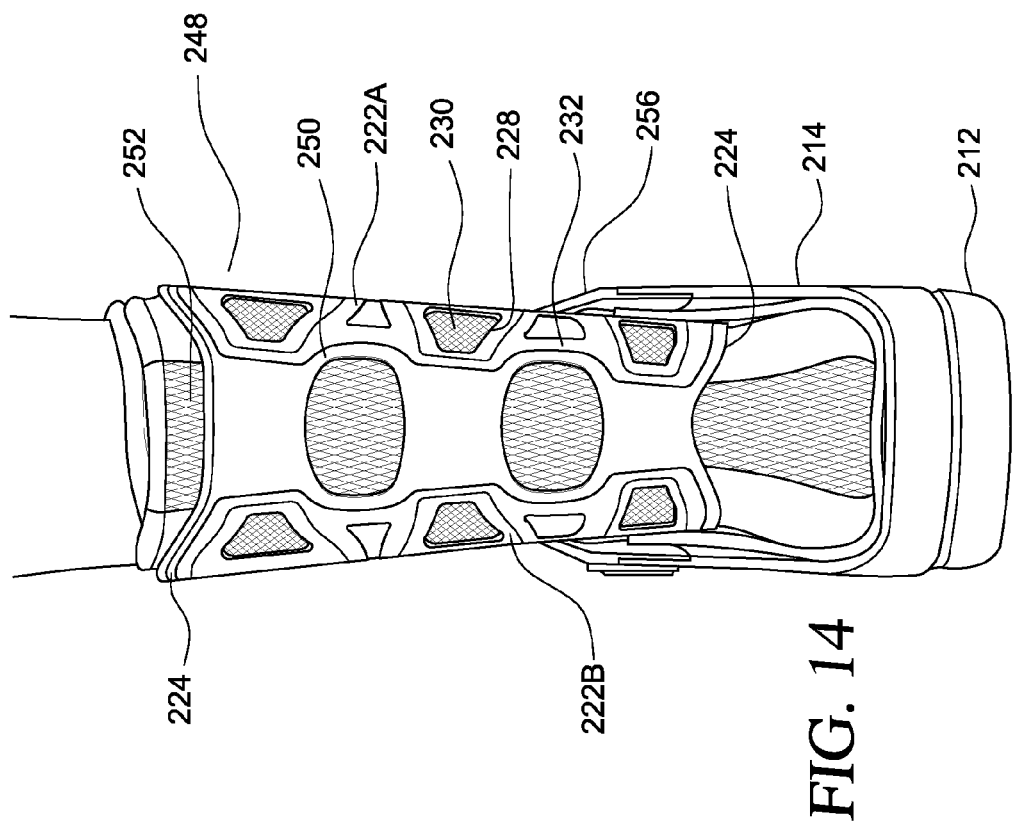
FIG. 14 is a rear elevational view of the walker of FIG. 12.
Figure 13:
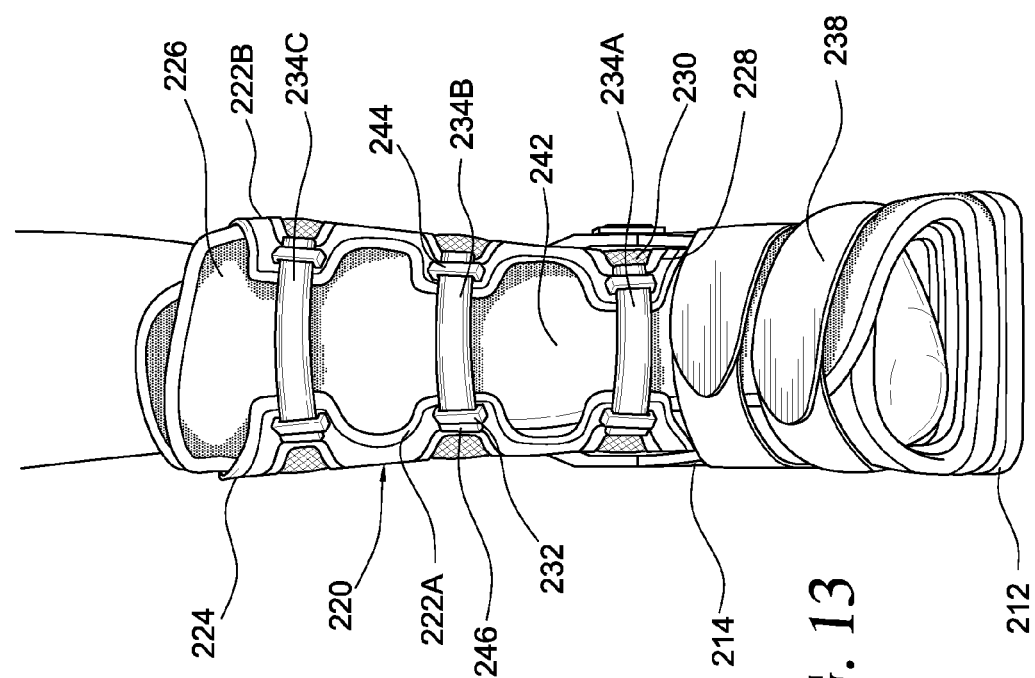
FIG. 13 is a front elevational view of the walker of FIG. 12.
Figure 15A:
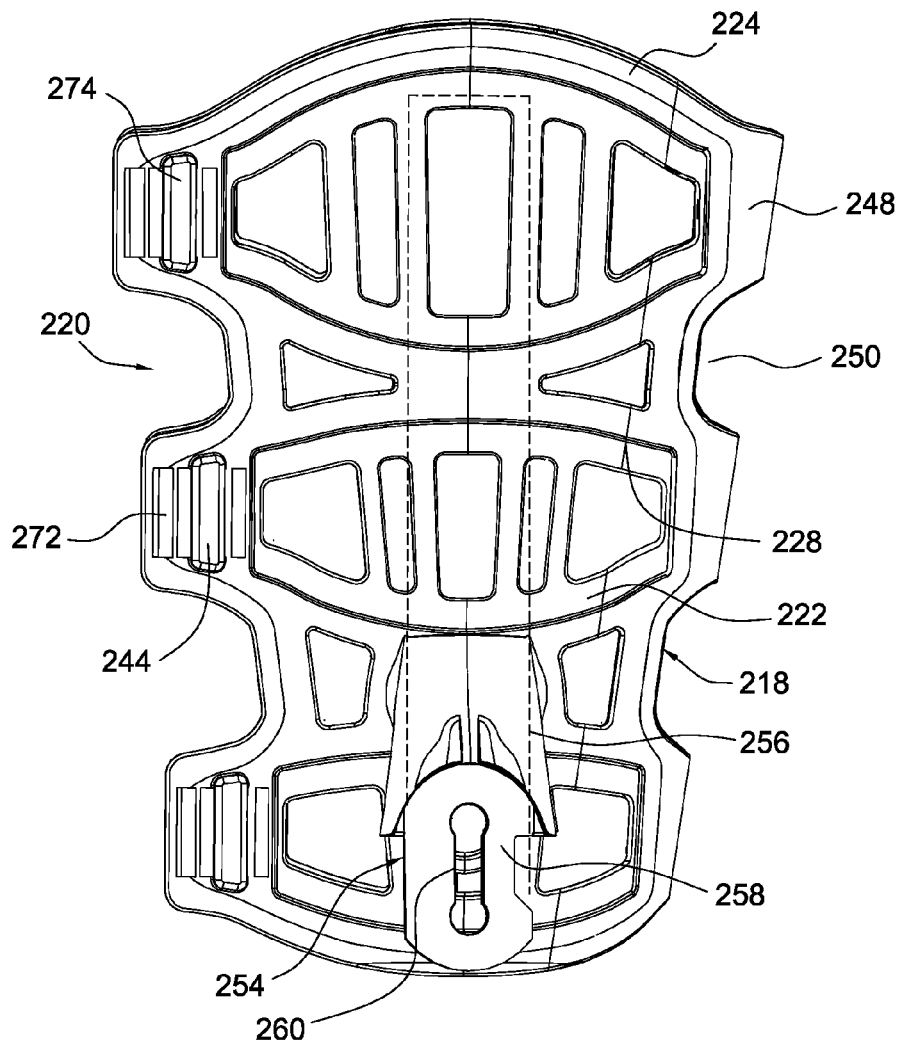
FIG. 15A is a side elevational view of the strut and shell assembly shown in FIG. 12.
Figure 16:
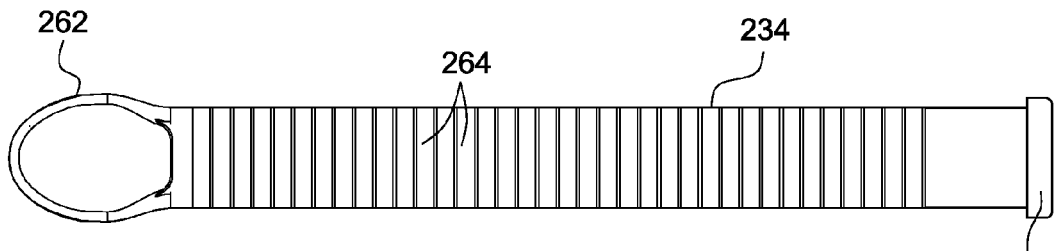
FIG. 16 is a top plan view of another embodiment of a tightening band.
Figure 17:
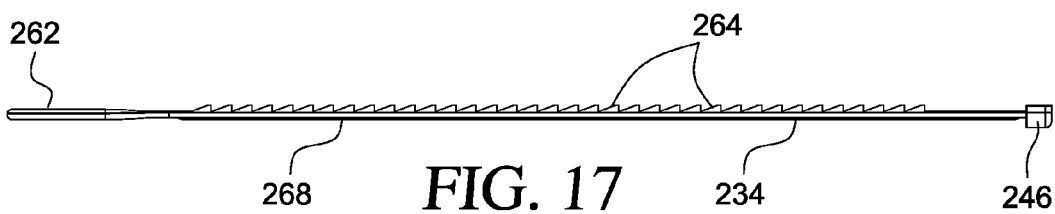
FIG. 17 is a side elevational of the tightening band of FIG. 16.
Figure 15B:
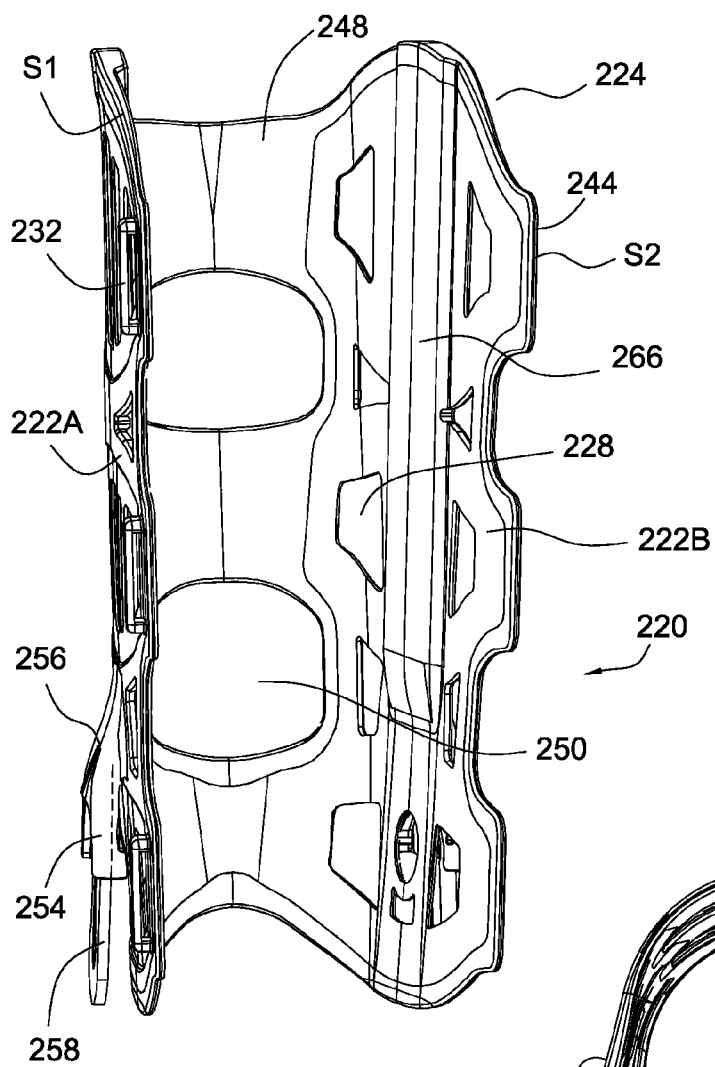
FIG. 15B is a front elevational view of the strut and shell assembly shown in FIG. 15A.
Figure 15C:
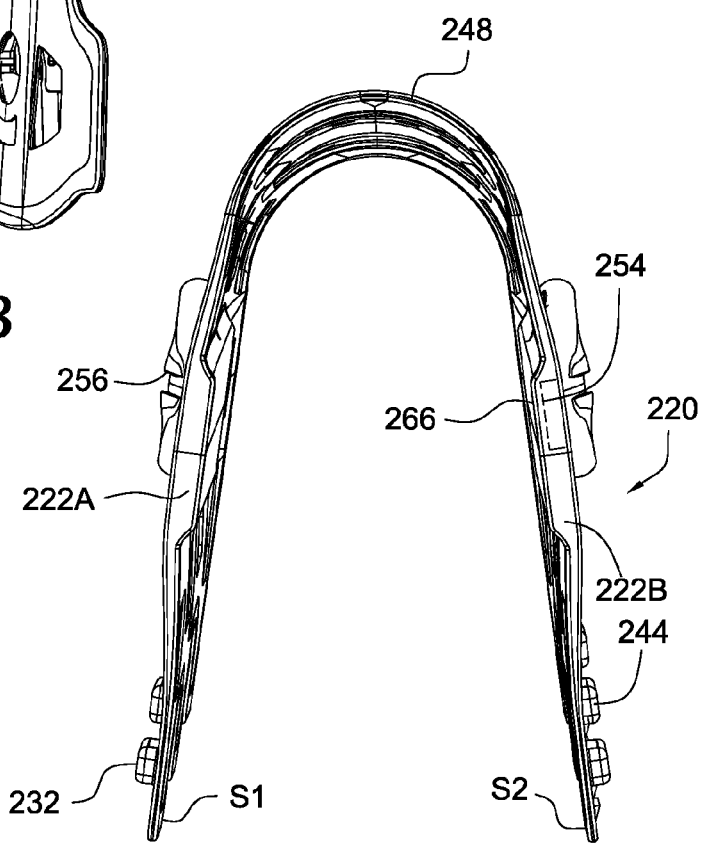
FIG. 15C is a top plan view of the strut and shell assembly of FIG. 15A.

Alternatively, as depicted in FIG. 11, a variation 136 of the strut is illustrated wherein the strut frame 138 and the resilient shell 142 are integrally molded as a unitary piece over an elongate frame member 140. While this embodiment does not include a hinge device, as in the embodiment of FIG. 10, it does include a locking mechanism 147 for embodiments of the walker wherein a hinge device is not employed. Suitable slots or apertures 146 may be formed in the shell to provide ventilation.

In accordance with another embodiment of the orthopedic device, FIGS. 12-18D exemplify the structure and the method of securing this embodiment of a walker onto a leg.

As illustrated in FIGS. 12-15C, the walker 200 has a strut support assembly 218 that extends vertically from and is hingedly connected (via lock mechanism 236) to side supports 216 of a base 214 of the walker. A typical configuration has a strut support assembly 218 that extends in an upright direction away from opposed sides of the base 214. The base 214 has a sole or foot receiving portion 212 that extends in the anterior and posterior directions, and is shaped and configured to receive and support a patient's foot therein. Straps 238 may extend between opposed sides of the base 214 and connect therewith by brackets 240.

The strut support assembly 218 also includes strut frame members 254 which may be embedded in, attached to or overmolded by the shell assembly 220, as taught by U.S. patent application publication 2007/0293798. The strut frame members 254 may cause the inner sides of the main shell bodies 222A, 222B to protrude as regions 266 along which the strut frame members 254 correspond, as exemplified in FIGS. 15B and 15C. In order to assist in pivotally moving the strut assembly 218 relative to the base 214, the strut assembly 218 defines flange portions 256 which extend from a lower side of the strut support assembly 218. The flange portions 256 define a clearance from a shell assembly 220 of the strut support assembly 218.

The strut frame members 254 define a connecting lower end 258 which includes a slot 260 for forming part of the locking mechanism 236. A locking mechanism 236 that may be used with this walker 210 is described in U.S. provisional application 60/960,782 filed on Oct. 15, 2007, and U.S. application Ser. No. 12/149,047, filed on Apr. 25, 2008, herein incorporated by reference.

A soft good support 226 is retained by the sole portion 212, base 214 and strut support assembly 218. The soft good support 226 may include a perforated section 252 formed as a strip along the rear portion of the strut support assembly 218. The soft good support 226 may be formed in any manner taught by those patents and publications incorporated herein by reference.

The strut support assembly 218 includes a resilient shell assembly 220 having a pair of shell main bodies 222A, 222B (generally as "222") and a border portion 224 surrounding the periphery of the shell assembly 220. The border portion 224 is preferably secured to the main bodies 222 by way of overmolding, much in the same manner as taught in U.S. patent application publication 2007/0293798. Alternatively, the border portion 224 may be secured to the main shell bodies 222 in any one of the ways taught in U.S. patent application publication 2007/0293798.

A connective rear portion 248 connects the main shell bodies 222A, 222B. The connective rear portion 248 is preferably more flexible than the main bodies 222, and may be formed continuously with the border portion 224. Accordingly, the rear and border portions have greater flexibility properties than the main shell bodies 222. The shell assembly 220 also forms a front clearance 242 between the opposed first and second sides S1, S2 which permits entry of a leg therein. Because of the flexibility of the rear portion and resiliency of the main shell bodies 222, the first and second sides S1, S2 may be drawn towards one another so as to tightly secure the walker to the leg of the wearer.

The main shell bodies 222 define a plurality of openings 230 thereabout to ventilate the walker on the leg. Spacer material or ventilation features 230 may be provided on the soft good support 226, or attached to the shell assembly 220 so as to correspond to the openings 230. The rear portion 248 likewise defines openings 250 so as to enhance the flexibility, reduce weight and increase ventilation of the rear portion 248.

In observing FIGS. 15A-15B, 16 and 17, a tightening system in accordance with the walker embodiment 200 is shown. The shell assembly 218 defines a first side S1 on the first main shell body 222A having a first strap guide 232 through which a tightening band or strap 234 may be inserted. The tightening band 234 defines a base 246 at a first end which is sized larger than the first strap guide 232, and a second end having a handle 262 which may be deformed so as to pass through the first strap guide 232.

The shell assembly 218 defines a second side S2 located on the second main shell body 222B upon which a second strap guide 244 is located. A plurality of teeth 272 are formed through and on both sides of the second strap guide 232. These teeth 272 are engageable with a series of teeth 264 formed along a first side of the tightening band 234. The second strap guide 244 may also form elongate channels 274 which correspond to elongate ribs 268 formed along a second side of the tightening band 234 so as to guide the tightening band 234 through the second strap guide 244.

The combination of the teeth 272, 264 permits incremental and uni-directional adjustment and locking of the tightening band relative to the shell assembly. The base 246 serves as a uni-directional anchor which allows for the tightening band and the first side of the shell main body to be pulled together toward the second side of the shell main body. Once in place, the tightening band can only be removed by cutting since the combination of the teeth effectively form a ratcheting device.

FIGS. 18A-18D exemplify how the tightening band 234 is inserted and set in place on the shell assembly 220. FIG. 18A shows how the handle 262 is deformable so it can pass through the first strap guide 232. In this particular embodiment, the handle 262 forms a loop which permits a finger to tightly grasp and pull the tightening band 234 through the first strap guide 232, as illustrated in FIG. 18B.

FIG. 18C shows the tightening band 234 after the handle 262 has been pulled through the first strap guide 232. The elongate ribs 268 are shown which guide the tightening band 234 through both the first and second strap guides 232, 244, and indicia 276 is provided which may show sizing and a pulling direction denoted by, for example, an arrow. The teeth of the tightening band engage the teeth of the second main body thereby permitting the tightening band to only be drawn in the direction of the arrow of the indicia 276.

FIG. 18D illustrates that once the tightening band 234 has been fully pulled so as to draw the first and sides S1 and S2 towards one another according to the need of the wearer, the second end of the tightening band 234 may be cut 270 so as to reduce the portion of the tightening band 234 extending beyond the second strap guide 244 (including the handle 262). As such point, the tightening band can only removed if it is cut between the first and second strap guides 232, 244.

The disclosed embodiments of an orthopedic device in the exemplary form of a walker provide many improvements and allow easy access to a wound site located on the foot or ankle The invention provides a solution that entails one product that can be left on the lower limb of the user generally but still allows for visual inspection of a wound site. Other advantages are, for example, easier and faster access to wounds when conducting scheduled clinic, hospital, or home visits, an easily repeatable application on the limb which mitigates any special expertise (as compared to a TCC), and is a cheaper and reusable option over the TCC.

The disclosed embodiments allow removal of the base and/or sole of the walker, and thus there is no associated inconvenience of removing the entire walker during scheduled clinic, hospital, or home visits.

A further advantage is increased patient compliance of wearing the walker continuously, due to the forced compliance aspect, as well as the improved comfort and reduced bulk of the product.

The structure of the disclosed embodiments allows for the direct application of advanced dressings or pharmaceuticals that require frequent dressings changes to the wound site while still providing for a non-removable, at least by the patient, walker.

Further, due to the fact that appointment times or visit times can be reduced, and since casting materials do not need to be repeatedly removed, discarded and new casting materials applied, the disclosed embodiments provide a lower cost alternative to current TCCs. Further, the disclosed embodiments provide increased ease of use over current TCCs.

It is understood that the size of the disclosed embodiments and the components thereof can be adjusted so that different users having different sized legs, ankles, and feet may benefit from the present design. The patient compliance system may be also adapted for a variety of orthopedic devices adapted to be secured to the arm, shoulder, back, knee, hip or other anatomical portions of the wearer.

The width, thickness and length of the struts and sole members may be varied to accommodate different sized users. In particular, by providing separate tightening bands at both the anterior and posterior sides of the leg, one and incremental adjustment of the tightening bands can better adapt the walker to the specific geometry of a leg.

It is also understood that the embodiments disclosed may be assembled prior to applying the walkers to the patient's limb for the first time. Alternatively, portions of the walkers may be applied to the patient's limb and remaining portions may be subsequently attached to the portions maintained on the patient's limb. For example, strut and bases may be attached to the patient followed by connecting a removable sole to the strut and bases. Alternatively, a sole member may be attached to the patient's limb and strut members may be subsequently attached to the sole member and then to the patient's limb.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various features from different embodiments. For example different locking devices, hinging devices, brackets and tightening bands for securing with the brackets may be freely changed and substituted.

Although this invention has been disclosed in the context of certain exemplary embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

The invention claimed is:

1. An orthopedic device, comprising:
a base including a foot receiving portion and a side support extending from the foot receiving portion;
a strut assembly secured to the side support and including a hinge device located at a lower end and securing to the base, the hinge device having an elongate slot and openings at opposed ends of the slot, the openings having peripheries delimited by material of the hinge device outside of the slot;
a locking device arranged to lock movement of the base relative to the strut assembly and engaging the hinge device, the locking device being located at the hinge device and having a pivot point about which the strut pivots and slides relative to the side support via the slot and the openings of the hinge device with the peripheries about the openings preventing linear movement of the pivot point.

2. The orthopedic device according to claim 1, wherein the strut assembly includes a rigid or semi-rigid elongate portion.

3. The orthopedic device according to claim 2, wherein the strut assembly includes a resilient and flexible shell assembly secured to the elongate portion.

4. The orthopedic device according to claim 1, wherein the strut assembly includes a resilient and flexible shell assembly.

5. The orthopedic device according to claim 4, wherein the resilient shell assembly has at least one shell main body and a border portion surrounding a periphery of the shell main body.

6. The orthopedic device according to claim 5, wherein the border portion is secured to two main bodies and maintains the two main bodies in connection with one another.

7. The orthopedic device according to claim 5, wherein a connective rear portion connects main shell bodies located on opposed sides of the strut assembly from one another, the connective rear portion having a curvature and is more flexible than the main bodies.

8. The orthopedic device according to claim 7, wherein the connective portion is continuously formed with the border portion.

9. The orthopedic device according to claim 1, wherein the strut assembly defines at least one flange portion protruding outwardly from a lower side of the strut assembly, the at least one flange portion pivotally connecting to the base.

10. The orthopedic device according to claim 1, wherein the strut assembly includes an elongate strut frame and a shell detachably connected to the strut frame.

11. The orthopedic device according to claim 10, wherein the strut frame is rigid or semi-rigid and the shell is more flexible than the strut frame.

12. The orthopedic device according to claim 10, wherein the shell is connected to an inner surface of the strut frame, the shell extending along a substantial length of the strut frame.

13. The orthopedic device according to claim 1, wherein the strut assembly is composed of at least two portions each having a different flexibility.

14. The orthopedic device according to claim 1, wherein the strut assembly defines at least one strap guide and at least one tooth protruding from the strut assembly in correspondence with the strap guide.

15. An orthopedic device, comprising:
 a base including a foot receiving portion and a side support extending from the foot receiving portion;
 a strut assembly secured to the side support, the strut assembly including a rigid or semi-rigid strut frame, and at least two additional portions each having a different flexibility, the strut assembly further including a hinge device located at a lower end and securing to the base, the hinge device having an elongate slot and openings at opposed ends of the slot, the openings having peripheries delimited by material of the hinge device outside of the slot;
 a locking device arranged to lock movement of the base relative to the strut assembly and engaging the hinge device, the locking device being located at the hinge device and having a pivot point about which the strut pivots and slides relative to the side support via the slot and openings of the hinge device with the peripheries about the openings preventing linear movement of the pivot point.

* * * * *